(12) United States Patent
Taylor et al.

(10) Patent No.: US 7,188,526 B2
(45) Date of Patent: Mar. 13, 2007

(54) ULTRASONIC TRANSDUCER

(75) Inventors: Steven C. Taylor, Idaho Falls, ID (US); Nancy C. Kraft, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 146 days.

(21) Appl. No.: 11/172,129

(22) Filed: Jun. 29, 2005

(65) Prior Publication Data

US 2007/0000329 A1    Jan. 4, 2007

(51) Int. Cl.
*G01N 29/26* (2006.01)

(52) U.S. Cl. .............................. 73/618; 73/632; 73/643

(58) Field of Classification Search ................... 73/618, 73/620, 625, 626, 627, 628, 632
See application file for complete search history.

(56) References Cited

U.S. PATENT DOCUMENTS

| | | | |
|---|---|---|---|
| 3,978,712 A | 9/1976 | Cowan et al. | |
| 4,112,773 A | 9/1978 | Abts | |
| 4,917,096 A | 4/1990 | Englehart et al. | |
| 4,945,766 A | 8/1990 | Dahlmann et al. | |
| 5,099,693 A * | 3/1992 | Payne et al. ................... | 73/632 |
| 5,176,034 A | 1/1993 | Hazony et al. | |
| 5,299,458 A | 4/1994 | Clark, Jr. et al. | |
| 5,381,693 A | 1/1995 | Kobayashi et al. | |
| 5,381,695 A * | 1/1995 | Payne et al. ................... | 73/643 |
| 5,406,850 A * | 4/1995 | Bouchard et al. ............. | 73/620 |
| 5,481,917 A | 1/1996 | Arima et al. | |
| 5,635,619 A | 6/1997 | Udpa et al. | |
| 5,963,882 A | 10/1999 | Viertl et al. | |
| 6,122,967 A | 9/2000 | Sword | |
| 6,125,704 A | 10/2000 | Wang | |
| 6,230,568 B1 | 5/2001 | Winston et al. | |
| 6,546,803 B1 | 4/2003 | Ptchelintsev et al. | |
| 6,739,196 B2 * | 5/2004 | Leybovich ................... | 73/620 |
| 6,757,948 B2 | 7/2004 | Ptchelintsev et al. | |

OTHER PUBLICATIONS

U.S. Appl. No. 10/803,518, Mar. 17, 2004, Taylor.

* cited by examiner

*Primary Examiner*—Hezron Williams
*Assistant Examiner*—Jacques M. Saint-Surin
(74) *Attorney, Agent, or Firm*—Wells St. John P.S.

(57) ABSTRACT

An ultrasonic transducer having an effective center frequency of about 42 MHz; a bandwidth of greater than 85% at 6 dB; a spherical focus of at least 0.5 inches in water; an F4 lens; a resolution sufficient to be able to detect and separate a 0.005 inch flat-bottomed hole at 0.005 inches below surface; and a beam size of approximately 0.006–0.008 inches measured off a 1½ mm ball in water at the transducer's focal point.

24 Claims, 5 Drawing Sheets

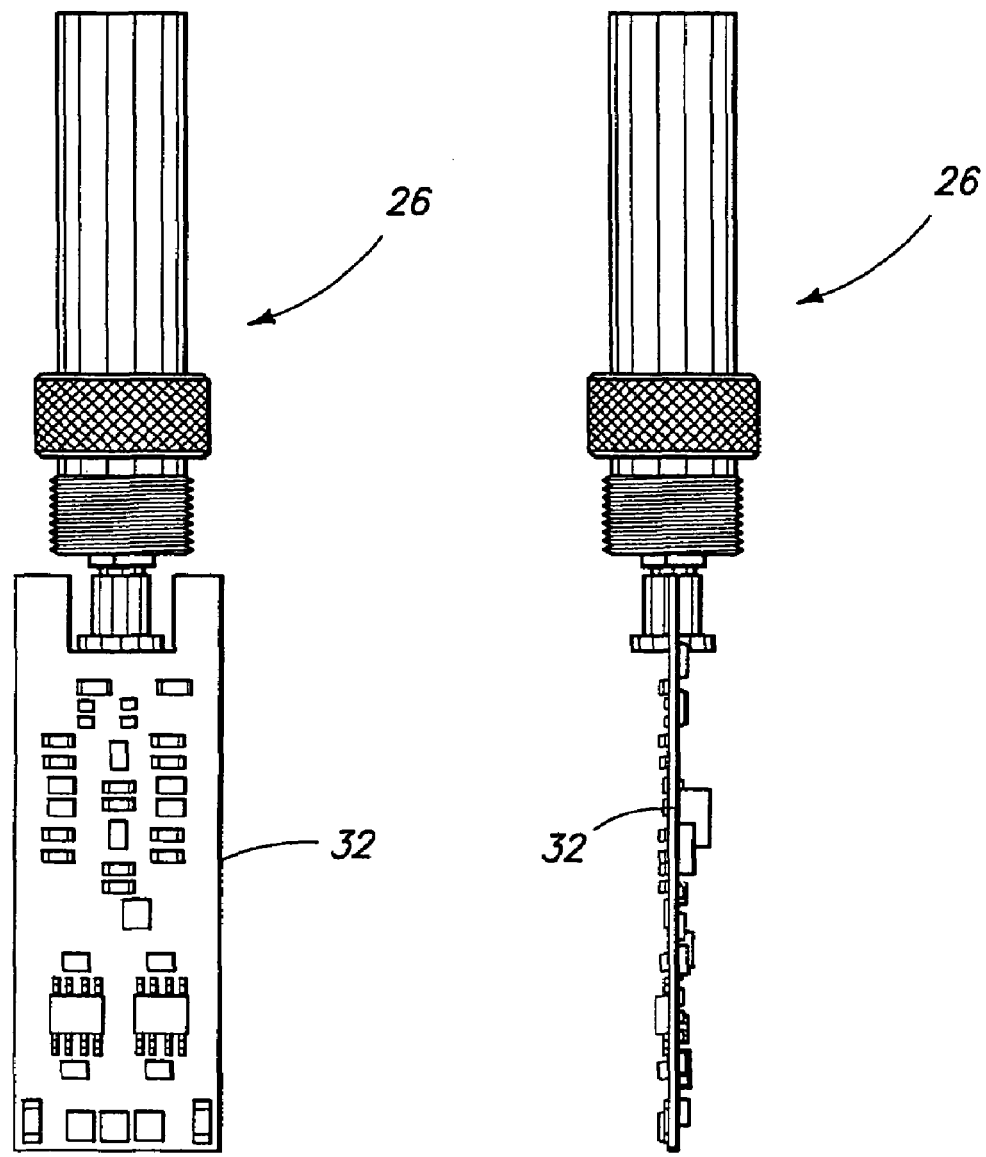

ULTRASONIC TRANSDUCER

GOVERNMENT RIGHTS

This invention was made with Government support under Contract DE-AC07-05ID14517 awarded by the U.S. Department of Energy. The Government has certain rights in the invention.

TECHNICAL FIELD

The invention relates to data acquisition methods and apparatus. Some aspects of the invention relate more particularly to ultrasonic testing methods and apparatus, including ultrasonic transducers.

BACKGROUND OF THE INVENTION

Ultrasonic transducers are useful for various applications, including ultrasonic testing methods. Ultrasonic testing equipment is used in a variety of applications such as for measuring flow, determining flaws, measuring thickness, and gauging corrosion. This equipment is used with a variety of materials such as metals, plastics, glass, liquids, and chemicals. One particular type of ultrasonic testing apparatus is a pulser-receiver that uses an ultrasonic transducer.

An ultrasonic transducer includes a crystal, wires from the crystal to a connector, and a lens.

Typical ultrasonic transducers operate in the range of about 500 kHz to 25 MHz. A small diameter beam is difficult to obtain with a good depth of field.

If it is desired to, for example, find a particle in a plate that is 50–100 thousandths of an inch thick, using a flat transducer having a beam of ¼ inch diameter or even a smaller straight beam having beam of ⅛ inch diameter, it is difficult to see a particle that is, for example one thousandth of an inch in diameter (0.001 inch diameter). Even if the particle is found, it is difficult to know where the particle is within the beam.

With a plate (e.g., Aluminum 6061) that is 50 thousandths of an inch thick, and a beam having a focal point that is 4 thousandths diameter, it would take approximately 11 scans to cover the whole plate. This is calculated as follows. The first 5 thousandths of an inch is in a dead zone and can't be seen. 50 thousandths minus 5 thousandths equals 45 thousandths. 4 thousandths (diameter of the beam focal point) goes into 45 thousandths approximately 11 times. There is a 50% overlap, so it takes approximately 22 scans to cover the whole plate. It would be desirable to cover the whole plate with a single scan.

There is a need to have a high frequency ultrasonic transducer that is highly focused with a large depth of field (i.e., larger focal area than 4 thousandths of an inch), and a good depth of field to reduce or eliminate the need to rescan areas at different depths to obtain information at multiple depths.

BRIEF DESCRIPTION OF THE DRAWINGS

Preferred embodiments of the invention are described below with reference to the following accompanying drawings.

FIG. 4 is a front assembly view showing how a crystal is attached to the circuit board, in one embodiment, after assembly.

FIG. 5 is a side view showing how a crystal is attached to the circuit board, in one embodiment, after assembly.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Ultrasonic pulsers and receivers are known in the art and are disclosed, for example, in the following U.S. patents which are incorporated herein by reference: U.S. Pat. No. 6,757,948 issued to Ptchelintsev et al. on Jul. 6, 2004; U.S. Pat. No. 6,546,803 issued to Ptchelintsev et al. on Apr. 15, 2003; U.S. Pat. No. 6,230,568, issued to Winston et al. on May 15, 2001; U.S. Pat. No. 6,125,704, issued to Wang on Oct. 3, 2000; U.S. Pat. No. 6,122,967 issued to Sword on Sep. 26, 2000; U.S. Pat. No. 5,963,882 issued to Viertl et al. on Oct. 5, 1999; U.S. Pat. No. 5,635,619 issued to Udpa et al. on Jun. 3, 1997; U.S. Pat. No. 5,481,917 issued to Arima et al. on Jan. 9, 1996; U.S. Pat. No. 5,381,693 issued to Kobayashi et al. on Jan. 17, 1995; U.S. Pat. No. 5,299,458 issued to Clark Jr. et al. on Apr. 5, 1994; U.S. Pat. No. 5,176,034 issued to Hazony et al. on Jan. 5, 1993; U.S. Pat. No. 4,917,096 issued to Englehart et al. on Apr. 17, 1990; U.S. Pat. No. 4,945,766 issued to Dahlmann et al. on Aug. 7, 1990; U.S. Pat. No. 4,112,773 issued to Abts on Sep. 12, 1978; and U.S. Pat. No. 3,978,712 issued to Cowan et al. on Sep. 7, 1976. Attention is also directed to the following commonly assigned application, which is incorporated herein by reference: U.S. patent application Ser. No. 10/803,518, filed Mar. 17, 2004, entitled "Ultrasonic Pulser-Receiver", by inventor Steven C. Taylor.

Figure 1:
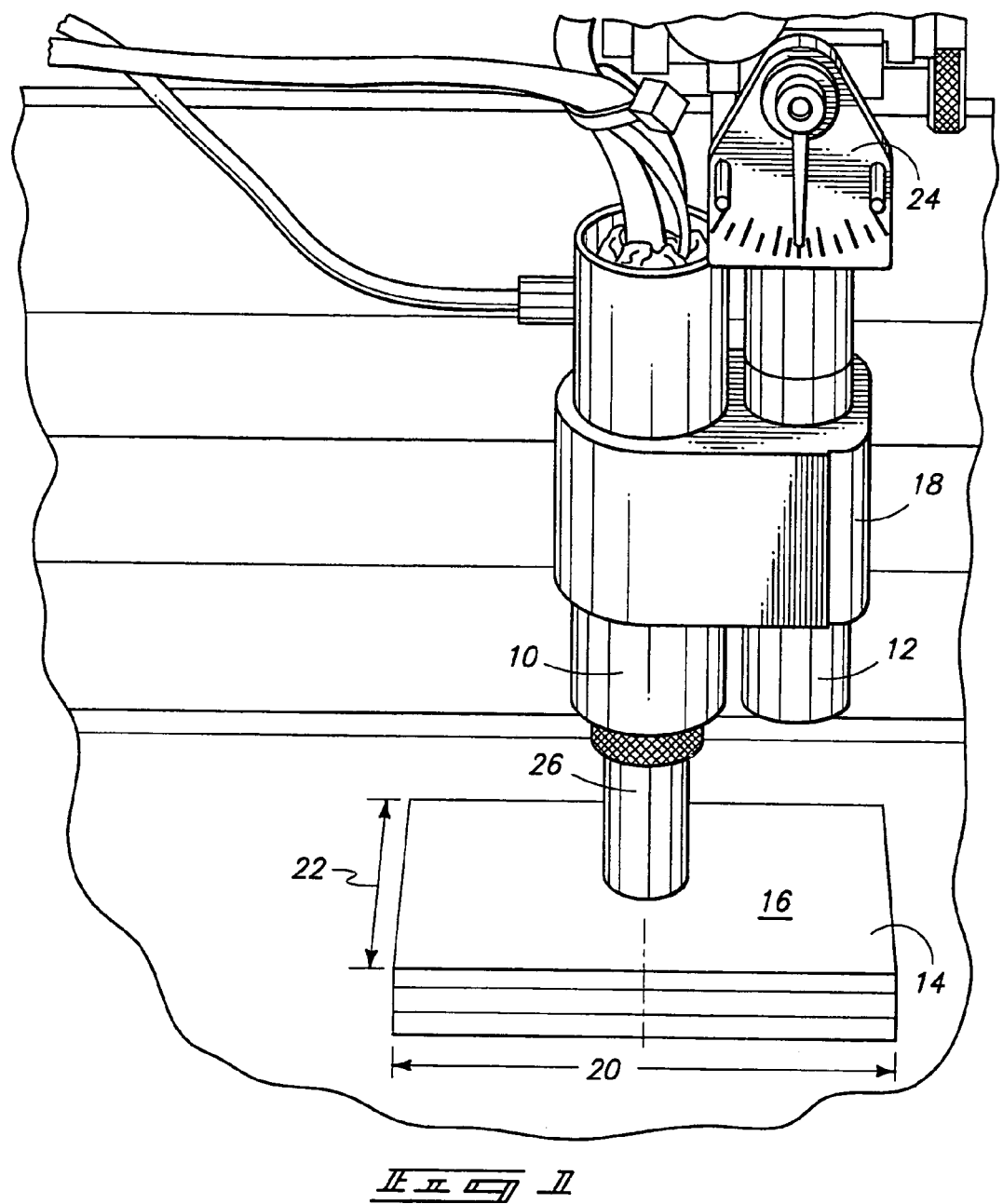
FIG. 1 is a perspective view showing a pulser and receiver in accordance with various aspects of the invention.

FIG. 1 shows an ultrasonic pulser and receiver 10 for inspecting an object 14 under inspection. In the illustrated embodiment, the ultrasonic pulser and receiver 10 are movable relative to the object 14. More particularly, in the illustrated embodiment, the pulser and receiver 10 are moveable together at least along an x-axis 20 and possibly also along a y-axis 22. For example, in the illustrated embodiment, the pulser and receiver 10 are movable along tracks (not shown) above the pulser and receiver 10, supported, for example, by a support tube or member 12. The pulser and receiver 10 and are held, for example, in a holder 18 that includes parallel generally cylindrical apertures which receive the pulser and receiver 10. In the illustrated embodiment, a transducer positioning or alignment tool 24 is provided. Aspects of the invention relate to a high frequency ultrasonic transducer, used in the pulser 10, having certain specifications. Alternative embodiments are possible, depending on the application. However, at least some of the specifications are particularly valuable for certain applications, as will become clearer from a review of the specifications, and reasons for the specifications, that will be provided below.

In some embodiments, the focused transducer has a 4 microsecond depth of field centered at 19 microseconds plus 2 microseconds and minus 2 microseconds or from 17 microseconds to 21 microseconds. In some embodiments, beam diameter is 0.006 to 0.008 inches. The FFT at 19 microseconds is approximately 42 MHz, and has a frequency bandwidth of 85%.

More particularly, in some embodiments, the transducer has an effective center frequency at 19 microseconds-water path, not less than 42 MHz. 19 microseconds is equivalent to about ½ inch of water. It is useful to have a high frequency transducer function at nearly ½ inch of water away from the object 14 being examined because, in some embodiments, there are obstacles that the transducer has to physically move past, and if the transducer was any closer to the object being examined, it could hit nuts and bolts or other obstacles in the object under inspection, and break. In some embodiments, the object under inspection is inspected while it is under water. This could be useful, for example, if the object contains or may contain radioactive material. The object being examined, in some embodiments, is not a smooth plate that is extended out. In some embodiments, it is held in a frame, and that frame has to have a certain amount of hardware to support it because it is a fairly large size. That is the reason behind the 19 microseconds, or ½ inch of water path, specification. In some embodiments, the transducer works at plus or minus 2 microseconds from the 19 microsecond specified center frequency. In other words, in some embodiments, the transducer's depth-of-field is centered at 19 microseconds plus 2 microseconds and minus 2 microseconds or from 17 microseconds to 21 microseconds. Other embodiments are possible. For example, the transducer may be centered to be a greater distance from the object being examined, or a smaller distance if less clearance is required in a given application.

In ultrasonic non-destructive testing, use of higher frequencies result in tighter resolution. If a low frequency is used, the time between cycles is many milliseconds. As frequency increases, the time between the cycles gets smaller. At 42 MHz, this frequency allows the ultrasound signal to dampen after one full cycle, which is equivalent to 40 nanoseconds. While other materials could be inspected, in aluminum it is equivalent to five mils of aluminum. In various embodiments, it is useful to be able to inspect at five mils. So a frequency of 42 MHz is a useful number for that reason.

A high bandwidth is preferred, for the transducer 10, in various embodiments of the invention. More particularly, in the illustrated embodiment, the transducer has a bandwidth greater than 85%. When the transducer 10 is excited, a wide variety of frequencies are generated, and they are very high frequencies. It is difficult to obtain good resolution with lower than 85% of the bandwidth at 6 db. There is a tradeoff between gain and bandwidth. In some embodiments, the inventor prefers bandwidth to gain. Thus, in the illustrated embodiment, the transducer 10 has a bandwidth that is greater than 85% at 6 db.

With regard to focus, in some embodiments, the transducer is spherically focused at approximately ½ inch of water. The ½ inch in the water relates back to the 19 microsecond center frequency, and there is some tolerance either way. As discussed above, there is, for example, up to a plus or minus 2 microseconds variance either way in time in relationship to the ½ inch. However, in some embodiments, it is useful to be out ½ inch or nearly ½ inch away from the object 14 under inspection. For example, in some embodiments, there is like a bolt sticking out about ⅜ of an inch from the object under inspection. Thus, in the illustrated embodiment, the pulser has a focus that is spherical, at approximately 0.5 inches in water.

The transducer includes or is defined by a piezoelectric crystal (not shown) that has an infinite or open circuit impedance, but when it is excited, the impedance changes, and it is desired to drive the transducer into 50 Ohms. The pulser-receiver disclosed in U.S. patent application Ser. No. 10/803,518 has a 50 Ohm matching resistor. Therefore, it is desired to match the transducer onto the circuit board. Even though the crystal does not have a resistor in it, it is on the circuit board. In the preferred embodiment, a connector comes out of the crystal and goes directly onto the board. Therefore, there is no separate cable or anything else between the crystal and the circuit board to cause reflections or any standing waves that may interfere with data.

Thus, in some embodiments, a specification is that no electrical impedance matching circuit be required between the crystal and the circuit board.

In the illustrated embodiment, the circuit board is about two and a half inches long and about an inch wide. Other dimensions are possible.

With regard to depth of field, there are typically two types of transducers that could be purchased off the shelf (if an off-the-shelf transducer were to be used). One type has a flat beam that goes out the front and has a standard diameter, such as ¼ inch diameter, ⅛ inch diameter, 1 inch diameter, 5 inches diameter, or any other diameter. This type diverges at 1.2 degrees. The beam diameter is much bigger than a small object that it would be desirable to be able to detect. This type of transducer has very low resolution and is not used, in the preferred embodiment.

A second type of transducer includes focused transducers. Typically, and dependent on the frequency used, a focused transducer focuses on a very small spot. At the frequencies used in the preferred embodiment, the spot at the focal point is typically no bigger than about 4 thousands of an inch wide or tall.

In the preferred embodiment, it is desired to be able to look for particles at anywhere from, for example, five thousandths or six thousandths of an inch under the top surface 16 of the object under inspection. The ultrasonic signal has to have time to ring down, and then flat line.

In the illustrated embodiment, it is desirable to look under the surface 16 at, for example, five thousandths or six thousandths of an inch down through ten thousandths of an inch to look for particles. In one embodiment, the object under inspection 14 is an aluminum block, and the particles that it is desired to detect are radioactive particles, such as uranium particles. However, the invention has application to methods and apparatus for detecting any small particles or reflectors.

Thus, in the preferred embodiment, it is desirable not to have to use a servo or cause the transducer to step up and down to be able to look at a range of depths (e.g., from five to ten thousandths of an inch below the top surface 16 of the object 14) under inspection. It is desirable to have a depth of field, like in a camera.

Figure 2:
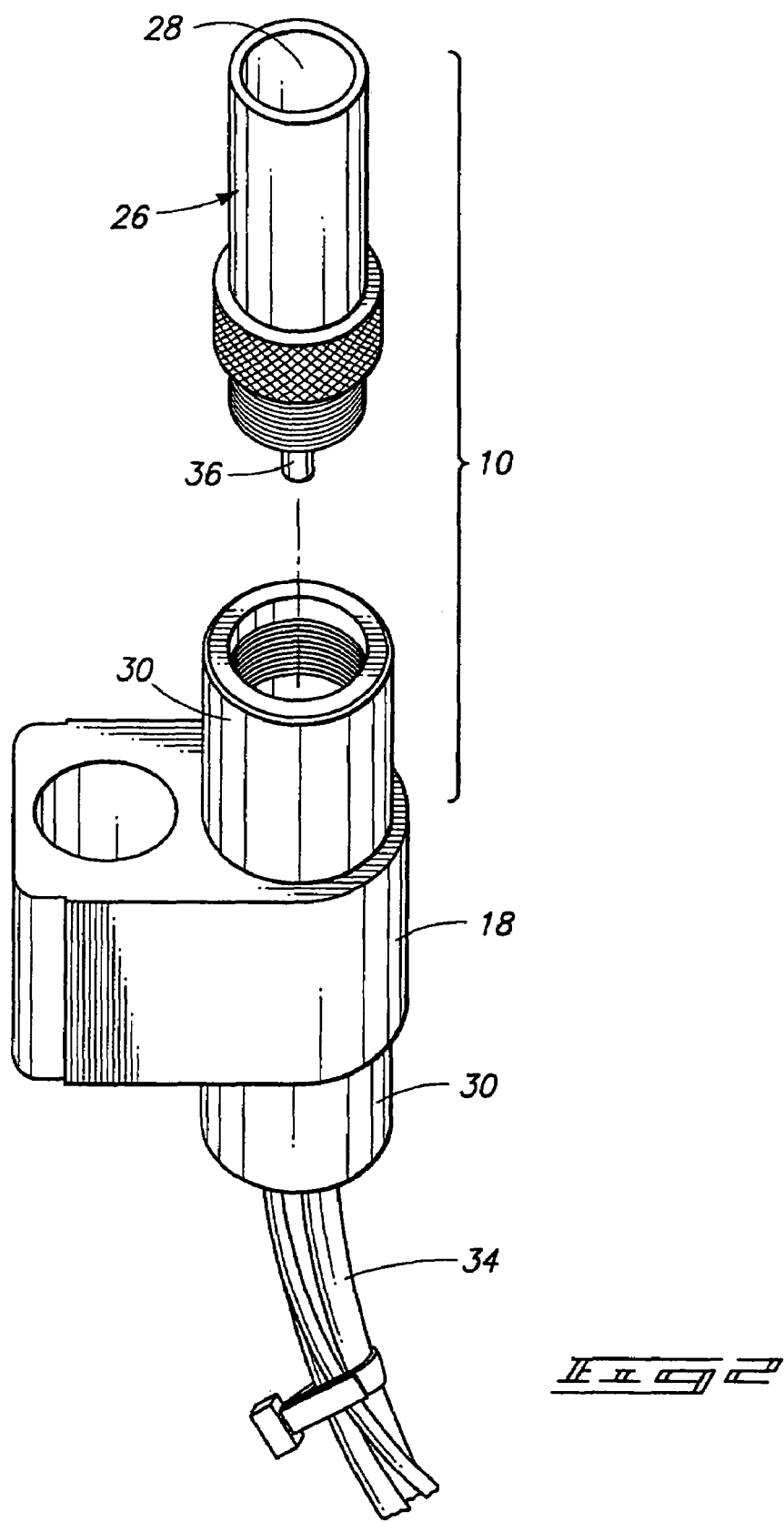
FIG. 2 is a perspective view showing the pulser of FIG. 1 upside down.

Therefore, in the illustrated embodiment, the transducer has an F4 lens 28 (see FIG. 2) providing a depth of field of +/−0.1 inches from the focal point, in water, measured at −6 dB. In alternative embodiments, the depth of field is at least +/−0.1 inches in aluminum from the focal point.

In the preferred embodiment, the transducer has a resolution sufficient to detect and separate 5000th of an inch flat bottomed hole at 5000 inch below the surface. In the preferred embodiment, it is desired to be able to look for particles that are between ½ thousands of an inch in diameter, up to 1½ thousands of an inch in diameter. In alternative embodiments, smaller resolution is possible as long as it is possible to detect particles that are between ½ thousands of an inch diameter to 1½ thousands of an inch in diameter. The size of the particles is known, in the preferred embodiment. More particularly, in manufacture of certain object 14, such as 6061 aluminum blocks, particles go through sieves, such as 200 mesh sieves, and there will be a percentage of particles that are 200 mesh, a percentage that is ¾ of that, a percentage that is ½ of that, etc. Thus, in the preferred embodiment, the transducer has a resolution providing an ability to detect and separate a 0.005 inch flat-bottomed hole at 0.005 inches below the top surface of 6061 aluminum block.

Beam size is a parameter of interest because, if beam size is too large, there will not be sufficient resolution. Beam size is typically expressed as a size measured off of a 1½ millimeter ball. A very small beam size is desired, the smaller, the better. In the preferred embodiment, beam size is approximately 0.006–0.008 inches measured off a 1½-mm ball in water at the transducer's focal point.

Acoustic noises can cause big problems in ultrasonic testing. Whenever a piezoelectric crystal is excited, a sound wave doesn't just go out the front. There is a sound wave that goes out the sides, out the back corners, and elsewhere. It is therefore useful to control the sound beam. In the preferred embodiment, backing is put on the back of the crystal. The backing can include, for example, fine particles of carbide or some other material that has high impedance, held together, for example, by epoxy. As sound goes out the back, it goes into the epoxy and hits the particles and bounces until it goes away (dispersed).

With regard to the sides, a sound wave will hit the side and it will bounce back and forth going sideways until it finds a critical angle where it can start bouncing around. Eventually it will hit something, and come out at an undesired location or time. It is preferred that all energy exit the front of the crystal. Antennas can be matched to a desired frequency. Similarly, with ultrasonics, a coating can be put on the front of the crystal to match it to water.

This allows more energy out at a desired frequency. The coating also has a tendency to dampen waves that are bouncing around inside the crystal. Thus, in the illustrated embodiment, a crystal is provided having acoustic noises of no more than 5% full screen amplitude following the primary cycle of a glass plate reflection @ 19 microseconds. In the illustrated embodiment, there are about 6 microseconds of flat signal area there where there is no acoustic noise.

There is a downshift in water. If the transducer starts out at about 100 MHz, for example, for every millimeter of water that this high frequency sound wave travels through, there is about a 5% downshift in frequency (not attenuation, but a change in frequency called a downshift) at frequencies above about 25 MHz. This is a phenomenon that is well documented in literature related to ultrasonic testing. This downshift is accommodated by expecting back a frequency that is different from the frequency that is sent out.

Figure 3:
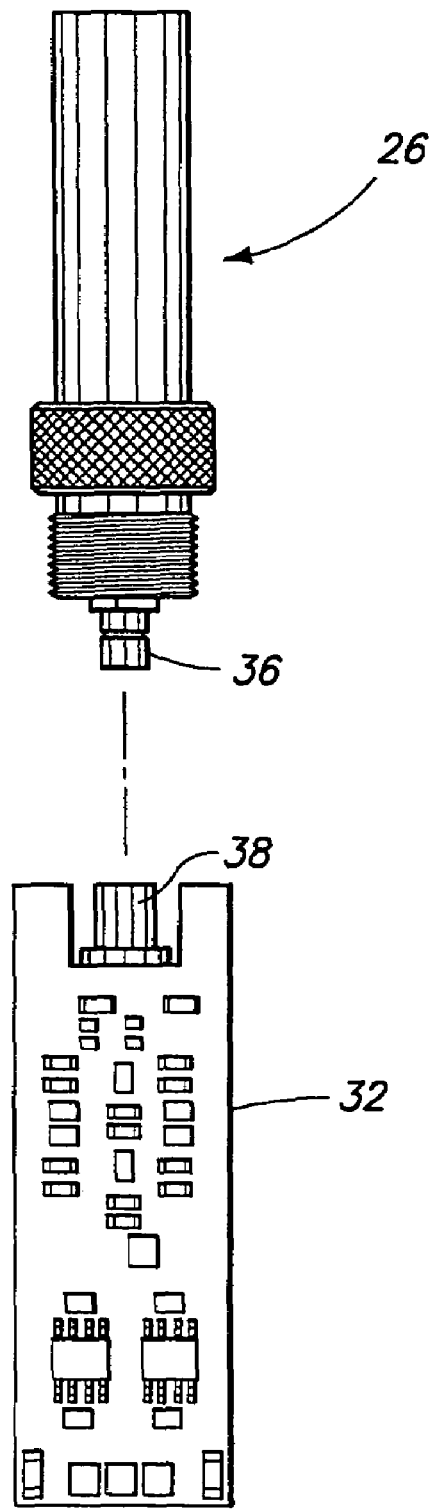
FIG. 3 is a front assembly view showing how a piezoelectric crystal is attached to a circuit board, in one embodiment, prior to assembly.

The ultrasonic pulser 10 includes (see FIG. 2) a portion 26 including an ultrasonic crystal (not shown), and including F4 lens 28. The pulser 10 also includes a portion 30 which houses a circuit board 32 (see FIG. 3). The circuit board 32 includes circuitry for driving the crystal. Cables 34 allow for power and control signals to be provided to the circuit board 32 from a remote location or remote control station. The crystal has a standard UHF connector 36 on its back, used, in the illustrated embodiment, only for a mechanical mount.

There is no electrical signal going through the connector, in the preferred embodiment. It is a Connex connector, in the illustrated embodiment.

Thus, there is a portion of a Connex connector on the back of the crystal that mates with a mating portion 38 (see FIG. 3) of the connector that is provided on the circuit board 32. The circuit board 32 is housed in the portion 30. Thus, in the preferred embodiment, the connector employed is a standard case with UHF for a mechanical Connex connector. In the illustrated embodiment, the transducer signal/Connex connector is to be centered to +0.002-inches of the transducer centerline. FIG. 4 is a front assembly view showing how a crystal is attached to the circuit board, in one embodiment, after assembly. FIG. 5 is a side view showing how a crystal is attached to the circuit board, in one embodiment, after assembly.

Figure 6:
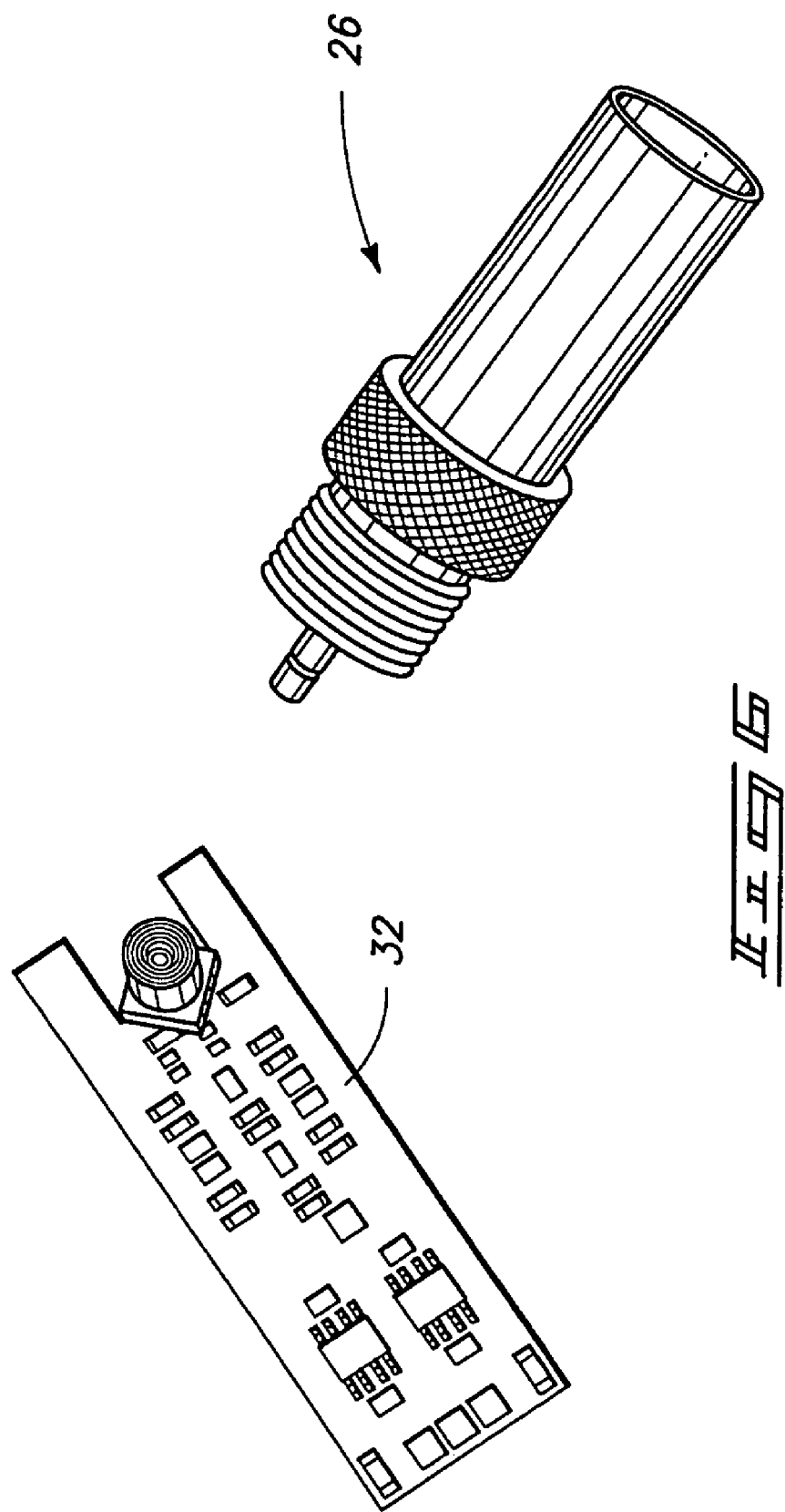
FIG. 6 is a side view showing how a crystal is attached to the circuit board, in one embodiment, after assembly, in an alternative embodiment, in which the crystal extends generally perpendicular to the circuit board.

FIG. 6 is a side view showing how a crystal is attached to the circuit board, in one embodiment, after assembly, in an alternative embodiment, in which the crystal extends generally perpendicular to the circuit board 32. In this embodiment, the portion 30 would have to be oriented differently to be able to house the circuit board 32.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. An ultrasonic transducer having:
   an effective center frequency of about 42 MHz;
   a bandwidth of greater than 85% at 6 dB;
   a spherical focus of at least 0.5 inches in water;
   an F4 lens;
   a resolution sufficient to be able to detect and separate a 0.005 inch flat-bottomed hole at 0.005 inches below surface; and
   a beam size of approximately 0.006–0.008 inches measured off a 1½ mm ball in water at the transducer's focal point.

2. An ultrasonic transducer in accordance with claim 1 having acoustic noises of no more than 5% full screen amplitude following the primary cycle of a glass plate reflection @ 19 microseconds.

3. An ultrasonic transducer in accordance with claim 1 wherein the transducer is a focused transducer.

4. An ultrasonic transducer in accordance with claim 1 and including a crystal physically coupled to a Connex UHF connector.

5. An ultrasonic transducer in accordance with claim 1 wherein the F4 lens provides a depth of field of at least +/−0.1 inches from the focal point in water, measured at −6 dB.

6. An ultrasonic transducer in accordance with claim 1 and capable of finding a particle as small as one thousandth of an inch in diameter in a plate that is about 50–100 thousandths of an inch thick in a single scan.

7. An ultrasonic transducer in accordance with claim 1 and having a spherical focus of about 0.5 inches in water.

8. An ultrasonic transducer in accordance with claim 1 and mounted for movement with an ultrasonic receiver.

9. A method of manufacturing an ultrasonic transducer, the method comprising providing an ultrasonic transducer having:
- an effective center frequency of about 42 MHz;
- a bandwidth of greater than 85% at 6 dB;
- a spherical focus of at least 0.5 inches in water;
- an F4 lens;
- a resolution sufficient to be able to detect and separate a 0.005 inch flat-bottomed hole at 0.005 inches below surface; and
- a beam size of approximately 0.006–0.008 inches measured off a 1½ mm ball in water at the transducer's focal point.

10. A method in accordance with claim 9 wherein the transducer has acoustic noises of no more than 5% full screen amplitude following the primary cycle of a glass plate reflection @ 19 microseconds.

11. A method in accordance with claim 9 wherein the transducer is a focused transducer.

12. A method in accordance with claim 9 and including a crystal physically coupled to a Connex UHF connector.

13. A method in accordance with claim 9 wherein the F4 lens provides a depth of field of at least +/−0.1 inches from the focal point in water, measured at −6 dB.

14. A method in accordance with claim 9 wherein the transducer is capable of finding a particle as small as one thousandth of an inch in diameter in a plate that is about 50–100 thousandths of an inch thick in a single scan.

15. A method in accordance with claim 9 wherein the ultrasonic transducer has a spherical focus of about 0.5 inches in water.

16. A method in accordance with claim 9 and further comprising mounting the transducer for movement with an ultrasonic receiver.

17. A method of nondestructive inspection of 6061 aluminum blocks, the method comprising:
mounting an aluminum block for inspection;
providing an ultrasonic transducer movable over the aluminum block, the ultrasonic transducer having:
- an effective center frequency of about 42 MHz;
- a bandwidth of greater than 85% at 6 dB;
- a spherical focus of at least 0.5 inches in water;
- an F4 lens;
- a resolution sufficient to be able to detect and separate a 0.005 inch flat-bottomed hole at 0.005 inches below surface; and
- a beam size of approximately 0.006–0.008 inches measured off a 1½ mm ball in water at the transducer's focal point.

18. A method in accordance with claim 17 wherein the transducer has acoustic noises of no more than 5% full screen amplitude following the primary cycle of a glass plate reflection @ 19 microseconds.

19. A method in accordance with claim 18 wherein the transducer is a focused transducer.

20. A method in accordance with claim 19 and including a crystal physically coupled to a Connex UHF connector.

21. A method in accordance with claim 20 wherein the F4 lens provides a depth of field of at least +/−0.1 inches from the focal point in water, measured at −6 dB.

22. A method in accordance with claim 21 wherein the transducer is capable of finding a particle as small as one thousandth of an inch in diameter in a plate that is about 50–100 thousandths of an inch thick in a single scan.

23. A method in accordance with claim 22 wherein the ultrasonic transducer has a spherical focus of about 0.5 inches in water.

24. A method in accordance with claim 23 and further comprising mounting the transducer for movement with an ultrasonic receiver.

* * * * *